United States Patent
Yan et al.

(10) Patent No.: US 9,739,700 B2
(45) Date of Patent: Aug. 22, 2017

(54) METHOD FOR DETECTING NANO-PARTICLES USING A LENS IMAGING SYSTEM WITH A FIELD STOP

(71) Applicant: XIAMEN UNIVERSITY, Fujian (CN)

(72) Inventors: Xiaomei Yan, Fujian (CN); Shaobin Zhu, Fujian (CN)

(73) Assignee: NANOFCM, INC., Fujian (CN)

( * ) Notice: Subject to any disclaimer, the term of this patent is extended or adjusted under 35 U.S.C. 154(b) by 64 days.

(21) Appl. No.: 14/434,914

(22) PCT Filed: Sep. 3, 2013

(86) PCT No.: PCT/CN2013/082860
§ 371 (c)(1),
(2) Date: Apr. 10, 2015

(87) PCT Pub. No.: WO2014/056372
PCT Pub. Date: Apr. 17, 2014

(65) Prior Publication Data
US 2015/0233812 A1    Aug. 20, 2015

(30) Foreign Application Priority Data
Oct. 12, 2012    (CN) .......................... 2012 1 0391585

(51) Int. Cl.
*G01N 15/14*    (2006.01)
*G01N 21/85*    (2006.01)

(52) U.S. Cl.
CPC ......... *G01N 15/1434* (2013.01); *G01N 21/85* (2013.01); *G01N 2201/06113* (2013.01)

(58) Field of Classification Search
CPC ............. G01N 33/587; G01N 33/5434; G01N 15/1434; G01N 15/14; G01N 15/1463; G01N 21/85
(Continued)

(56) References Cited

U.S. PATENT DOCUMENTS

2015/0346076 A1* 12/2015 Stramski ............ G01N 15/1434
356/336

FOREIGN PATENT DOCUMENTS

| CN | 201622228 U | 11/2010 |
|---|---|---|
| CN | 101943663 A | 1/2011 |
| EP | 0257559 A2 | 3/1988 |
| JP | H01129161 | 5/1989 |
| JP | 1991150445 | 6/1991 |

(Continued)

OTHER PUBLICATIONS

Lubbeck et al., "Microfluidic Flow Cytometer for Quantifying Photobleaching of Fluorescent Proteins in Cells", American Chemical Society 2012, pp. 3929-3937.
Zhu et al., "Single Nanoparticles and Viruses Detection and Characterization", (Abstract) Chinese Chemical Society, Apr. 13, 2012.
Yang, Lingling et al.; Development of an Ultrasensitive Dual-Channel Flow Cytometer for the Individual Analysis of Nanosized Particles and Biomolecules; Anal. Chem. vol. 81, pp. 2555-2563; Apr. 3, 2009.

(Continued)

*Primary Examiner* — Que T Le
(74) *Attorney, Agent, or Firm* — Wegman, Hessler & Vanderburg

(57) ABSTRACT

Disclosed is a method for detecting nano-particles, comprising the steps of (1) compressing a sample liquid to be tested into a sample liquid flow by hydrodynamic focusing using a sheath fluid; (2) irradiating a measuring light to the sample liquid flow, wherein a single nano-particle in the sample liquid flow is irradiated by the measuring light for a duration of 0.1-10 milliseconds; (3) defining the area in which the measuring light irradiates the sample liquid flow as a detecting area, and collecting light signals emitted from the area irradiated by the measuring light by a lens imaging system, and allowing the light signals collected by the lens imaging system to pass a field stop, so as to filter out the light signals outside the detecting area and enrich the light signals from the detecting area; and (4) subjecting the light signals enriched by the field stop to optoelectronic signal conversion. The method can achieve detection for nano-particles with a low refractive index and a particle size of 24-1000 nm as well as nano-scale gold particles with a particle size of 6.7-150 nm.

14 Claims, 7 Drawing Sheets

(58) Field of Classification Search
USPC .......... 250/221, 222.2, 573–576, 208.1; 356/70–73, 336–343; 359/385–389, 368
See application file for complete search history.

(56) References Cited

FOREIGN PATENT DOCUMENTS

| | | |
|---|---|---|
| JP | 2003004625 | 1/2003 |
| JP | 2007024569 | 2/2007 |
| JP | 2009115672 | 5/2009 |
| JP | 2009536727 | 10/2009 |
| JP | 2011505578 | 2/2011 |

OTHER PUBLICATIONS

Zarrin, F. et al.; Effect of Sample Stream Radius upon Light Scatter Distributions Generated with a Gaussian Beam Light Source in the Sheath Flow Cuvette; Anal. Chem., vol. 59, No. 6, pp. 846-850; Mar. 15, 1987.
International Search Report dated Nov. 21, 2013 for corresponding patent application No. PCT/CN2013/082860.
Slootweg, Erik et al.; Fluorescent T7 display phages obtained by translational frameshift; Nucleic Acids Research, 2006, vol. 34, No. 20; Oct. 13, 2006.
Hartlen, Kurtis D. et al.; Facile Preparation of Highly Monodisperse Small Silica Spheres (15 to >200 nm) Suitable for Colloidal Templating and Formation of Ordered Arrays; Langmuir 2008, 24, 1714-1720; Jan. 29, 2008.

\* cited by examiner

METHOD FOR DETECTING NANO-PARTICLES USING A LENS IMAGING SYSTEM WITH A FIELD STOP

CROSS-REFERENCE TO RELATED APPLICATIONS

This application is a national phase of International Patent Application No. PCT/CN2013/082860 filed Sep. 3, 2013, which is incorporated herein by reference in its entirety, and which claims the priority filing benefit of Chinese Patent Application No. 201210391585.5 filed Dec. 12, 2012.

FIELD OF THE INVENTION

The present invention relates to the instrumental analysis field, in particular to a method for detecting nano-particles.

BACKGROUND OF THE INVENTION

As nano-biotechnology was developed rapidly in recent years, artificially synthesized nano-particles with unique structures and functions have taken an increasingly important role in the biomedical field, including targeted drug delivery, high-resolution tumor imaging, and disease diagnosis, etc., and in other fields, such as protein purification, biochemical analysis, food safety, and environmental monitoring, etc. The measurement of size distribution of functional nano-particles is of great importance for quality control and actual application of nano-particles. In addition, there are various biological nano-particles in the natural world, such as bacteria, viruses, organelles, molecular assemblies, etc. Quick and high-resolution nano-particle detection techniques will provide powerful analytical means for pathogen identification, quality control of viral vaccines, measurement of transduction efficiency of gene transfer viral vectors, and research of basic life science.

Nano-particles can be analyzed effectively by means of high-sensitivity flow cytometry. For example, in some literatures (Anal. Chem. 2009, 81, 2555-2563 and J. Am. Chem. Soc. 2010, 132, 12176-12178), a technical solution of high-sensitivity flow cytometry is disclosed, comprising: compressing a sample liquid to be detected into a sample liquid flow by hydrodynamic focusing with a sheath fluid, and irradiating measuring light to the sample liquid flow, wherein the volume of the sample liquid flow subjected to the irradiation of the measuring light is approx. 800 fL and 150 fL; collecting the scattered light and/or fluorescent light emitted from the nano-particles in the sample liquid flow via an aspheric lens and obtaining signals, and analyzing the nano-particles according to the signals. However, the technical solution disclosed in the technical literatures can only detect polystyrene nano-particles in particle size greater than 100 nm, but can't detect smaller nano-particles with lower-refractivity. For nano-particles, the intensity of scattered light is attenuated at a rate proportional to sixth-power of particle size, i.e. when the particle size is halved, the signal strength will be decreased by 64 times. Therefore, it is difficult to detect nano-particles with smaller particle size.

SUMMARY OF THE INVENTION

The object of the present invention is to provide a method for detecting nano-particles with smaller particle size.

To attain this object, the present invention provides a method for detecting nano-particles, comprising the following steps: (1) compressing a sample liquid to be detected into a sample liquid flow by hydrodynamic focusing using a sheath fluid, wherein the sample liquid flow contains nano-particles to be detected, and the nano-particles are essentially separated from each other and essentially flow in the same line in the sample liquid flow; (2) irradiating a measuring light to the sample liquid flow, wherein a single nano-particle in the sample liquid flow is irradiated by the measuring light for 0.1-10 ms, preferably 0.2-2 ms; (3) defining the region of the sample liquid flow subjected to irradiation of the measuring light as a detecting region, and collecting light signals emitted from the region irradiated by the measuring light via a lens imaging system, and allowing the light signals collected by the lens imaging system to pass through a field stop, so as to filter out the light signals outside the detecting region and enrich the light signals from the detecting region; (4) subjecting the light signals enriched by the field stop to optoelectronic signal conversion, and acquiring the electrical signals of scattered light and/or fluorescent light emitted from each nano-particle in the sample liquid flow respectively; and (5) carrying out qualitative and/or quantitative analysis for the nano-particles according to the electrical signals.

With the technical solution described above, the method provided in the present invention can be used to detect low-refractivity nano-particles with 24-1,000 nm particle size (e.g. polystyrene and silicon dioxide nano-particles) and gold nano-particles with 6.7-150 nm particle size.

Other characteristics and advantages of the present invention will be further detailed in the embodiments hereunder.

DESCRIPTION OF THE DRAWINGS

The accompanying drawings are provided here to facilitate further understanding on the present invention, and constitute a part of this description. They are used in conjunction with the following embodiments to explain the present invention, but shall not be comprehended as constituting any limitation to the present invention. Among the drawings:

FIG. 6A1, FIG. 6B1, FIG. 6C1 and FIG. 6D1 show the detection results in the form of signal waveform diagrams of scattered light channels for the samples in examples 1-4 of 44 nm polystyrene nano-particles, 40 nm silicon dioxide nano-spheres, 10 nm gold nano-particles, and a sample of T7 bacteriophages, respectively;

FIG. 6A2, FIG. 6B2, FIG. 6C2 and FIG. 6D2 are frequency distribution histograms of peak area of scattered light for the samples in examples 1-4;

FIG. 10A1, FIG. 10B1, FIG. 10C1 and FIG. 10D1 show the detection results in the form of signal waveform diagrams of scattered light channels for the samples in examples 6-9 of 6.7 nm gold nano-particles, 10 nm gold nano-particles, 24 nm silicon dioxide nano-spheres, and 29 nm silicon dioxide nano-spheres respectively;

FIG. 10A2, FIG. 10B2, FIG. 10C2 and FIG. 10D2 are frequency distribution histograms of peak area of scattered light for the samples in examples 6-9.

| Brief Description of the Symbols | | |
|---|---|---|
| 1 Achromatic doublet lens | 2 Sample tube | 3 Objective |
| 4 Dichroic filter | 5 Band-pass filter | 6 Lens |
| 7 Photoelectric detector | 8 Edge filter | 9 Band-pass filter |
| 10 Lens | 11 Photoelectric detector | 12 Laser |
| 13 Sheath fluid | 14 Sample liquid flow | |

DETAILED DESCRIPTION OF THE EMBODIMENTS

Hereunder the embodiments of the present invention will be detailed, with reference to the accompanying drawings. It should be appreciated that the embodiments described here are only provided to describe and explain the present invention, but shall not be deemed as constituting any limitation to the present invention.

Figure 2A:
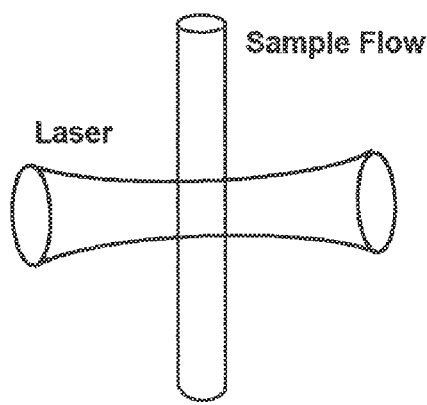
FIGS. 2A and 2B are schematic diagrams of a detecting region.
Figure 2B:
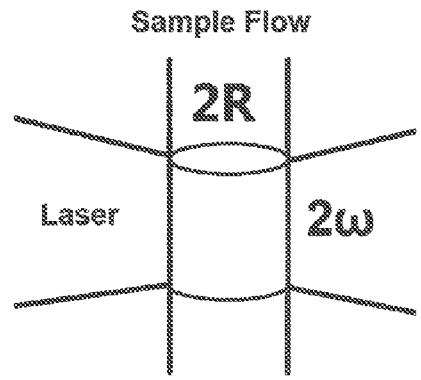

The present invention provides a method for detecting nano-particles, comprising the following steps: (1) compressing a sample liquid to be detected into a sample liquid flow by hydrodynamic focusing using a sheath fluid, wherein the sample liquid flow contains nano-particles to be detected, and the nano-particles are essentially separated from each other and essentially flow in the same line in the sample liquid flow; (2) irradiating a measuring light to the sample liquid flow, wherein a single nano-particle in the sample liquid flow is irradiated by the measuring light for 0.1-10 ms, preferably 0.2-2 ms; (3) defining the region of the sample liquid flow subjected to irradiation of the measuring light as a detecting region, and collecting light signals emitted from the region irradiated by the measuring light via a lens imaging system, and allowing the light signals collected by the lens imaging system to pass through a field stop, so as to filter out the light signals outside the detecting region and enrich the light signals from the detecting region; (4) subjecting the light signals enriched by the field stop to optoelectronic signal conversion, and acquiring the electrical signals of scattered light and/or fluorescent light emitted from each nano-particle in the sample liquid flow respectively; and (5) carrying out qualitative and/or quantitative analysis for the nano-particles according to the electrical signals.

Wherein the sheath fluid is any sheath fluid commonly used in flow cytometry, such as at least one of water, normal saline and phosphate buffer; preferably, water is used as the sheath fluid; more preferably, the water used as the sheath fluid is deionized water.

Wherein the hydrodynamic focusing has a conventional definition in flow cytometry, and particularly refers to the sheath fluid flows around the sample liquid, through which the sample liquid forms a liquid flow, i.e. a sample liquid flow, under the action of the sheath fluid.

Wherein the concentration of the nano-particles in the sample liquid may be regulated by conventional regulating method in the field of flow cytometry, so that the nano-particles are essentially separated from each other and essentially flow in the same line in the sample liquid flow.

Wherein the region of the sample liquid flow subjected to irradiation of the measuring light is defined as a detecting region. Specifically, as shown in FIG. 2, the region where the light beam of the measuring light superposes the sample liquid flow is the detecting region. Wherein the volume of the detecting region may be measured and calculated with a conventional method used in flow cytometer, such as the measurement and calculation method described in "Anal. Chem. 1987, 59, 846-850".

Specifically, the radius Rs of the sample liquid flow may be expressed by Equation I:

$$Rs = R\left[1 - \left(\frac{Q_{sheath}}{Q_{sample} + Q_{sheath}}\right)^{1/2}\right]^{1/2} \quad \text{Equation I}$$

In Equation I, $Q_{sheath}$ is the volumetric flow rate of the sheath fluid, $Q_{sample}$ is the volumetric flow rate of the sample liquid flow, and R is the equivalent radius of the cross section of the flow cell. For example, if the center of a flow cell is a square aperture with 250 μm side length, its equivalent circular channel with the same sectional area has a 141 μm radius. The flow velocity of the sheath fluid is 2.1 cm/sec, and the volumetric flow rate of the sample liquid flow is controlled at 5 nL/min. Thus, it can be calculated that the calculated sectional radius of the sample liquid flow is approx. 1.1 μm, i.e. Rs=1.1 μm.

If the radius ω of the laser spot is greater than the sectional radius R of the sample liquid flow, the detecting region will be essentially a cylinder in longitudinal direction, with a volume calculated as $2\pi R^2 \omega$. For example, if the laser beam is focused to a light spot with 16 μm radius, i.e. ω=8 μm, the sectional radius R of the sample liquid flow will be R=1.1 μm. The laser detecting region would be a longitudinal cylinder, with a volume approximately equal to 61 fL ($2\pi \times 1.1^2 \times 8\ \mu m^3$).

According to the method provided in the present invention, the volume of the detecting region may be 1-1,000 fL, preferably 10-100 fL, more preferably 10-30 fL. When the volume of the detecting region is 10-30 fL, the detection sensitivity and accuracy of the method provided in the present invention can be further improved.

According to the method provided in the present invention, the diameter of the sample liquid flow is 0.1-20 μm, preferably 0.5-5 μm, more preferably 1-3 μm. When the diameter of the sample liquid flow is 1-3 μm, the detection sensitivity and accuracy of the method provided in the present invention can be further improved.

According to the method provided in the present invention, the volumetric flow rate of the sample liquid flow is 0.1-100 nL/min, preferably 0.5-30 nL/min, more preferably 1-5 nL/min. When the volumetric flow rate of the sample liquid flow is 1-5 nL/min, the detection sensitivity and accuracy of the method provided in the present invention can be further improved.

According to the method provided in the present invention, the flow velocity of the sheath fluid is 0.5-10 cm/sec, preferably 1-3 cm/sec, more preferably 1.2-2.5 cm/sec. When the flow velocity of the sheath fluid is 1.2-2.5 cm/sec, the detection sensitivity and accuracy of the method provided in the present invention can be further improved.

According to the method provided in the present invention, the beam diameter of the measuring light is 1-150 times of the diameter of the sample liquid flow, preferably 2-50 times, more preferably 5-20 times. When the beam diameter of the measuring light is 5-20 times of the diameter of the sample liquid flow, the detection sensitivity and accuracy of the method provided in the present invention can be further improved.

According to the method provided in the present invention, the measuring light may be any measuring light commonly used in the field of flow cytometry, which is to say, those skilled in the art can select any laser with appropriate wavelength as the measuring light. For example, for gold nano-particles, usually laser with 530-550 nm wavelength is used as the measuring light; wherein, to further improve the S/N (signal-to-noise ratio) in the measurement and avoid the heating effect incurred by extremely high laser power, the intensity of the measuring light is preferably 0.05-8,000 kW/cm$^2$, more preferably 0.5-5,000 kW/cm$^2$, even more preferably 10-1,000 kW/cm$^2$ or 0.05-1,000 kW/cm$^2$.

According to the method provided in the present invention, the lens imaging system may be an infinity-corrected optical system or finity-corrected optical system. The infinity-corrected optical system may comprise infinite objective and imaging lens, and the finity-corrected optical system may comprise a finite objective. Wherein the infinite objective in the infinity-corrected optical system is commercially available, for example, the objective Olympus ULWD MSPlan 50×(0.55 N.A.) from Olympus; the imaging lens in the infinity-corrected optical system is commercially available, for example, the lens C240TM-A with 8 mm focal length from Thorlabs; the objective in the finity-corrected optical imaging system is commercially available, for example, the objective LPL 40×/0.65 160/1.5 from Nanjing Yifei Technology. To add optical elements into the imaging light path system more conveniently, preferably the lens imaging system is an infinity-corrected optical system.

Wherein the magnification factor of the infinite objective or finite objective may be 10-150 times, preferably 30-100 times, more preferably 50-100 times; the focal length of the imaging lens may be 1-1,000 mm, preferably 5-250 mm, more preferably 7.5-200 mm.

Wherein the real image may be formed in any appropriate direction; preferably, the real image is formed in a direction essentially perpendicular to the direction of the measuring light and the direction of the sample liquid flow. The image may be formed by scattered light, or by scattered light and fluorescent light.

According to the method provided in the present invention, the region subjected to irradiation of the measuring light may comprise a region of the sample liquid flow subjected to irradiation of the measuring light or a region of the sheath fluid subjected to irradiation of the measuring light. The light signals collected by the lens imaging system may comprise the light signals in the detecting region and may also comprise the light signals outside the detecting region. The purpose of filtering out the light signals outside the detecting region and enriching the light signals from the detecting region through a field stop is to carry out optical spatial filtering, which is equivalent to confining the detection range of the optical system using a field stop and thereby confining the region of photoelectric signal conversion.

Wherein the field stop may be a photosensitive region of the photoelectric detector or an aperture diaphragm added in front of the photoelectric detector.

Wherein the area of the photosensitive region or the aperture area of the aperture diaphragm is preferably 50 to 5×10$^6$ μm$^2$, more preferably 2×10$^3$ to 2×10$^5$ μm$^2$, even more preferably 8×10$^3$ to 8×10$^4$ μm$^2$.

According to the method provided in the present invention, the photoelectric signal conversion may be implemented with a variety of photoelectric detectors, which, for example, include but are not limited to avalanche photodiode, photomultiplier tube, silicon photodiode, charge coupling element or CMOS (complementary metal oxide semiconductor) device, and the photoelectric signal conversion preferably is implemented with an avalanche photodiode.

A photomultiplier tube (PMT) has advantages including high gain (with a 10$^6$ to 10$^7$ gain factor), large photosensitive region, and low dark current, etc., but has low quantum efficiency. For example, the PMT R928 from Hamamatsu usually has 1.3×10$^{-16}$ W Equivalent Input Noise (ENI).

An avalanche photodiode (APD) is a photodiode with an internal amplification function, and has a very small photosensitive region whose diameter is about 180 μm. An avalanche multiplication phenomenon of carriers occurs after incident photons being absorbed. The gain factor of an APD is usually 10$^2$ to 10$^3$. For example, the APDs SPCM-AQR-12 and SPCM-AQRH-14 from Perkin Elmer.

According to the method provided in the present invention, after the electrical signal is obtained, the method for qualitative and/or quantitative analysis of the nano-particles on the basis of the electrical signals can be a conventional method, for example, comparing the electrical signals of a blank sample and/or standard sample (including internal standard and external standard) with the electrical signals of the sample to be detected.

According to the method provided in the present invention, the particle size of the nano-particles is 1-1,000 nm, preferably 5-200 nm, more preferably 6.7-100 nm.

According to the method provided in the present invention, the nano-particles are artificially synthesized or natural nano-particles, and the natural nano-particles preferably are at least one type of biological nano-particles among prokaryotic cells, organelles, and viruses, etc.

Hereunder the present invention will be further detailed in examples.

Figure 4:
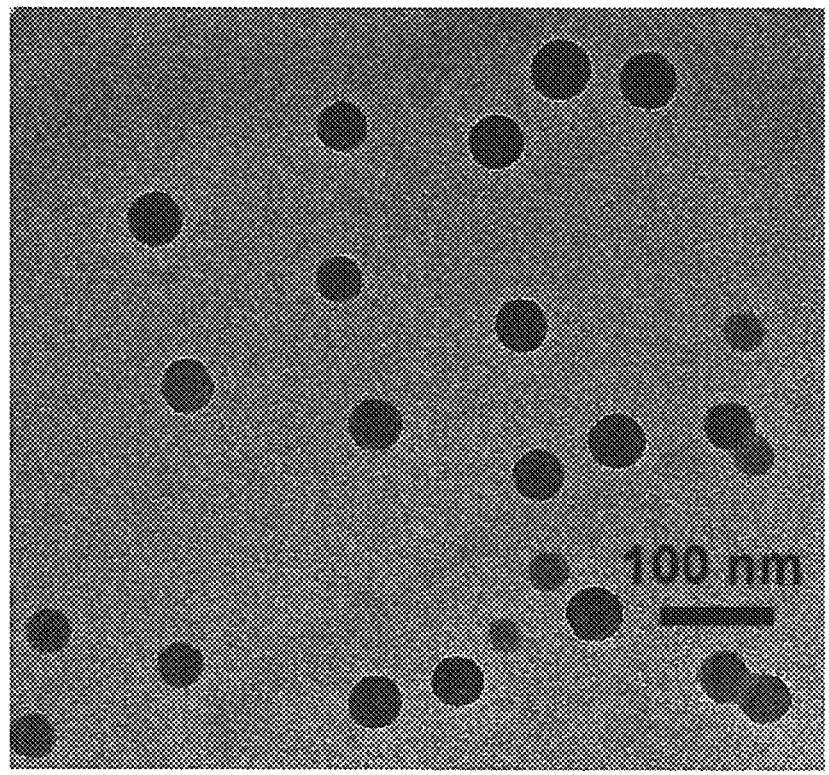
FIG. 4 is a Transmission Electron Microscopy (TEM) image of 44 nm polystyrene nano-spheres in example 1.
Figure 5:
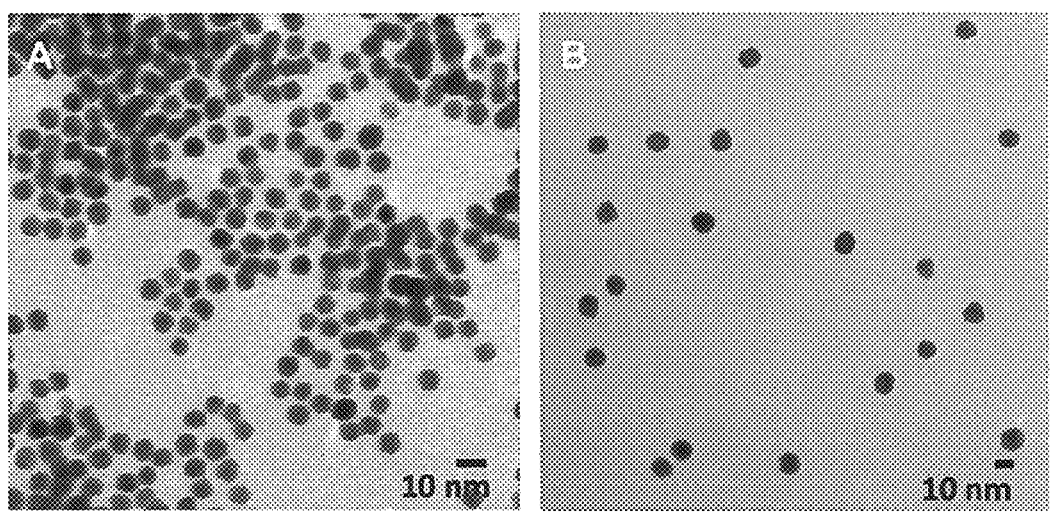
FIG. 5A is a TEM image of 6.7 nm gold nano-particles in example 6.
FIG. 5B is a TEM image of 10 nm gold nano-particles in examples 3 and 7.
Figure 7:
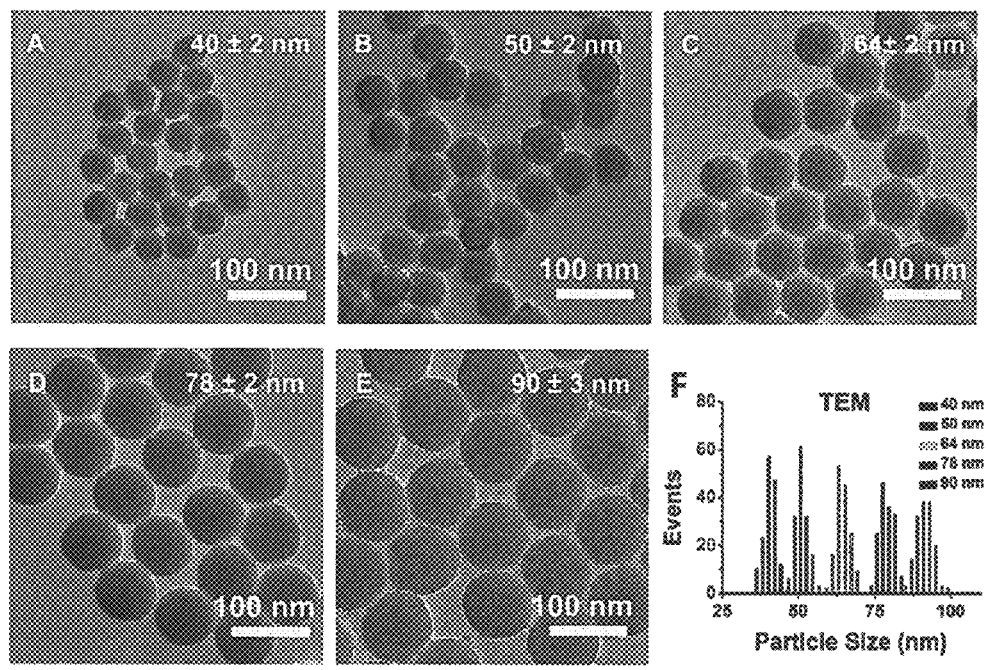
FIG. 7A shows a TEM image of 40 nm silicon dioxide nano-spheres in examples 2 and 5.
FIG. 7B shows a TEM image of 50 nm silicon dioxide nano-spheres in example 5.
FIG. 7C shows a TEM image of 64 nm silicon dioxide nano-spheres in example 5.
FIG. 7D shows a TEM image of 78 nm silicon dioxide nano-spheres in example 5.
FIG. 7E shows a TEM image of 90 nm silicon dioxide nano-spheres in example 5.
FIG. 7F shows particle average size and particle size distribution diagrams of each type of nano-particles obtained by performing statistics on the particle size of 150 nano-particles respectively.
Figure 9:
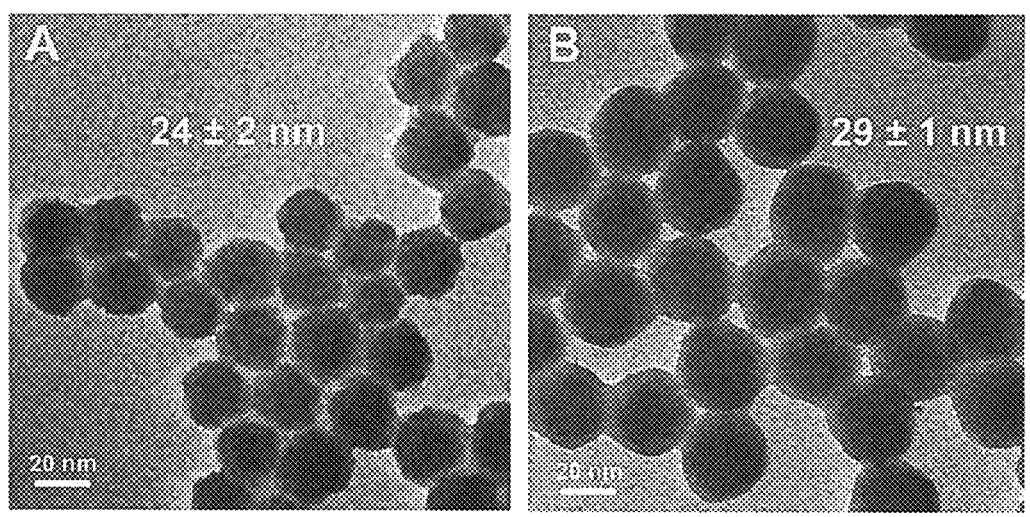
FIG. 9A shows a TEM image of 24 nm silicon dioxide nano-spheres in example 8.
FIG. 9B shows a TEM image of 29 nm silicon dioxide nano-spheres in example 9.

In the following examples, the polystyrene nano-spheres with 44 nm particle size are purchased from Spherotech (USA), and a TEM image of them is shown in FIG. 4. The gold nano-particles with particle size of 6.7 nm and 10 nm are purchased from nanoComposix (USA), and the TEM images of them are shown in FIG. 5. The silicon dioxide nano-spheres with particle size of 24 nm, 29 nm, 40 nm, 50 nm, 60 nm, 78 nm and 90 nm are synthesized with the method disclosed in "Langmuir, 2008, 24, 1714-1720", and the TEM images of them are shown in FIG. 7 and FIG. 9. The specific values of particle size of the nano-particles with known particle size are statistical average values measured by TEM method. The concentration of the polystyrene nano-spheres with 44 nm particle size and gold nano-particles with particle size of 6.7 nm and 10 nm are provided by the manufacturers, and the concentration of the synthesized silicon dioxide nano-spheres with particle size of 24 nm, 29 nm, 40 nm, 50 nm, 60 nm, 78 nm and 90 nm are values measured by a single particles counting method, see "J. Am. Chem. Soc. 2010, 132, 12176-12178" for the details of the method. T7 bacteriophages (with about 60 nm head diameter) are cultivated and purified with the method disclosed in "Nucleic Acids Res. 2006, 34, e137". The polystyrene nano-spheres with 44 nm particle size, silicon dioxide nano-spheres with different particle size of 24 nm, 29 nm, 40 nm, 50 nm, 60 nm, 78 nm and 90 nm, gold nano-particles with particle size of 6.7 nm and 10 nm, and T7 bacteriophages are diluted with ultra-pure water into suspension liquids at a concentration of $2\times10^9$ particles/mL respectively, and the suspension liquids are used as sample liquids to be detected.

Example 1

Figure 1:
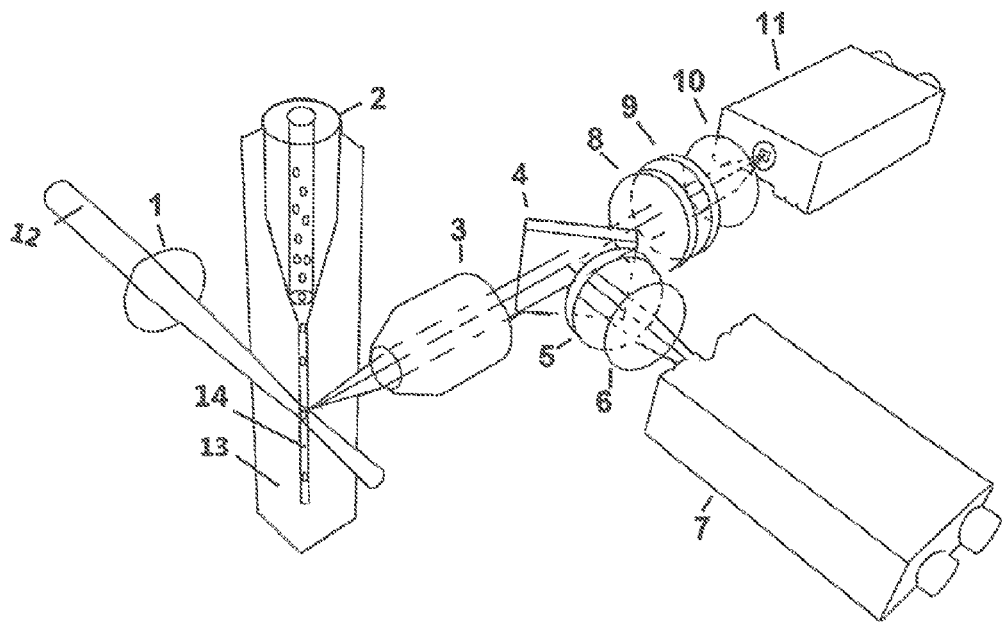
FIG. 1 is a schematic diagram of the light path in a preferred embodiment of the present invention.
Figure 3:
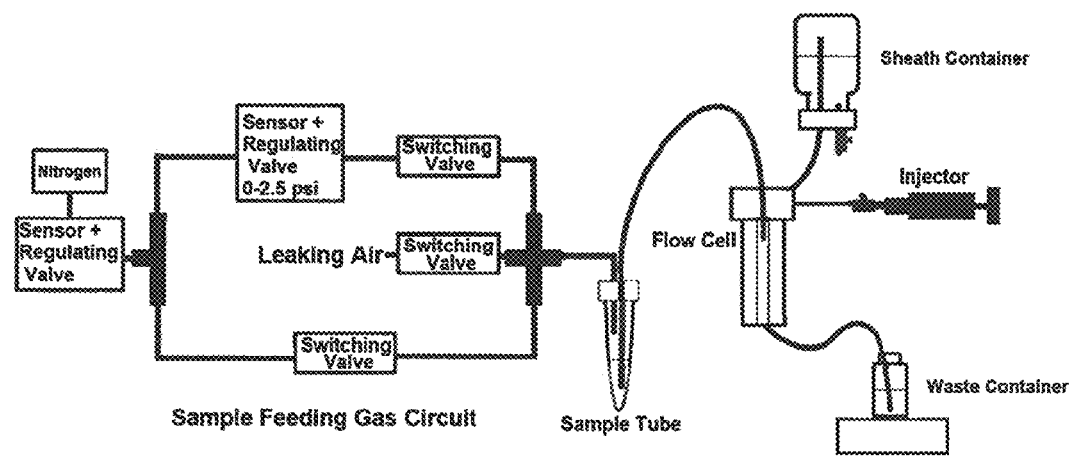
FIG. 3 is a schematic diagram of the liquid flow system in a preferred embodiment of the present invention.

With reference to the light path system shown in FIG. 1 and the liquid flow system shown in FIG. 3, a sample liquid to be tested (suspension liquid of polystyrene nano-spheres with 44 nm particle size at a concentration of $2\times10^9$ particles/mL) is pressed with nitrogen at 150 kPa pressure into an pressure-tight sample tube 2, and the pressure of the nitrogen is regulated so that the volumetric flow rate of the sample liquid is 2 nL/min. Wherein the sample tube is a quartz capillary tube with 40 μm inner diameter and 240 μm outer diameter, the terminal of the capillary tube is ground to an approx. 12° taper. The sample tube is inserted into a sheath fluid cavity from top to bottom in an axially parallel state, the sheath fluid cavity is a cuboid-shaped cavity formed by quartz glass, with 250 μm×250 μm cross section and 20 mm axial length, and the terminal of the sample tube is positioned at 8 mm above the top of the sheath fluid cavity in axial direction. A sheath fluid 13 flows from top to bottom at a flow velocity of 2 cm/sec in the sheath fluid cavity.

In a case that the flow velocity of the sheath fluid is 2 cm/sec and the volumetric flow rate of the sample liquid is 2 nL/min as calculated with the calculation method (as shown in Equation I) disclosed in "Anal. Chem. 1987, 59, 846-850", the sectional radius of the sample liquid flow 14 above the terminal of the sample tube is approx. 0.73 μm. Laser with 532 nm wavelength is focused through an achromatic doublet lens 1 (AC050-010-A1 from Thorlabs) into a laser beam 12 with 16 μm beam waist diameter, the irradiation intensity is 8 kW/cm² at the position of beam waist. At the position of beam waist of the laser beam 12, the axis of the laser beam 12 intersects with and is perpendicular to the axis of the sample liquid flow 14, and the laser beam 12 irradiates to a position at 150 μm below the terminal of the sample tube. Please see FIG. 2, suppose R is 0.73 μm and ω is 8 μm, then the calculated volume of the detecting region (i.e. a region of the sample liquid flow 14 subjected to irradiation of the measuring light (i.e. the laser beam 12)) is 26.8 fL, and the duration of irradiation of the measuring light on single nano-particle in the sample liquid flow is 0.8 ms.

Light signals emitted from the region subjected to irradiation of the measuring light is collected using an infinity-corrected optical system, which comprises objective 3, lens 6, and lens 10, wherein the objective 3 is Olympus ULWD MSPlan 50×(0.55 N.A.) from Olympus, and the lens 6 and lens 10 are C240TM-A from Thorlabs. Wherein the axis of the objective 3 in the infinity-corrected optical system is perpendicular to the axis of the laser beam 12 and the axis of the sample liquid flow 14. In the infinity-corrected optical system, the objective 3 and the lens 10 are coaxial, the axis of the lens 6 is perpendicular to and intersects with the axes of the objective 3 and lens 10, the point of intersection positioned between the objective 3 and the lens 10; a dichroic filter 4, a dichroic filter FF555-Dio2-25×36 from Semrock (USA), is arranged at the point of intersection, and it splits the light signals transmitted through the objective 3 into two branches, wherein the light with wavelength shorter than 555 nm (the light signals with such wavelength range is the scattered light from the tested polystyrene nano-spheres with 44 nm particle size) is reflected into the lens 6, while the light with wavelength longer than 555 nm (the light signals with such wavelength range is the fluorescent signals from the tested polystyrene nano-spheres with 44 nm particle size) is transmitted into the lens 10. A band-pass filter 5 (FF01-524/24-25 from Semrock) is arranged between the lens 6 and the dichroic filter 4, and is used to filter out scattered light with wavelength beyond 512-536 nm. An edge filter 8 (LP03-532RS from Semrock) is arranged between the lens 10 and the dichroic filter 4, and is used to remove the scattering background generated by the exciting light (i.e. remove light with 532 nm wavelength and transmit light with wavelength longer than 532 nm), and a filter 9 (FF01-579/34-25 from Semrock) is arranged between the lens 10 and the filter 8, and is used to filter out fluorescent light with wavelength beyond 562-596 nm.

The light with wavelength shorter than 555 nm reflected by the dichroic filter is detected by a photoelectric detector 7 after passing through the band-pass filter 5 and lens 6. Light signals of stray light from the sheath fluid and an optical window exist around the real image of the detecting region with R=0.73 μm and ω=8 μm, an APD (SPCM-AQRH-14) with a photosensitive region having 180 μm diameter is selected as the photoelectric detector 7, the photosensitive region of the APD is taken as the field stop, and optical calibration for the distance from the objective 3 to the sample liquid flow 14 and the spatial position of the photosensitive region is carried out, to filter out the light signals outside the detecting region and enrich the light signals in the detecting region. After optical correcting, the light signals received in the photosensitive region of the APD would be the light signals enriched by the field stop; finally, the light signals received in above photosensitive region of the APD is subjected to photoelectric conversion.

Wherein, in the process of optical calibration, when the output signal from the APD indicates that the intensity of the scattered light from the nano-particles is the strongest and the S/N is the best, it is deemed that the distance from the objective 3 to the sample liquid flow 14 and the spatial position of the photosensitive region of the APD are optimal, i.e. the purpose of the optical calibration has been attained and the optical calibration process has been completed. Wherein the magnification factor of the detecting region via the lens imaging system depends on the focal length of the objective 3 and lens 6, and the size of the detecting region multiplied by the magnification factor of the imaging system is equal to the spot size in the focal plane, i.e. the minimum spot size. The light signals of the detection region is focused by the lens 6, and on a plane parallel to the focal plane of the lens 6, the spot size of the detecting region varies continuously with the distance from such plane to the lens 6. By adjusting the spatial position of the APD, the spot size of the detecting region matches the size of the photosensitive region of APD, and the center of the spot of the detecting region superposes the center of the photosensitive region of the APD, thus the intensity of the scattered light from the nano-particles will be the strongest and the S/N will be the best.

Figure 6:
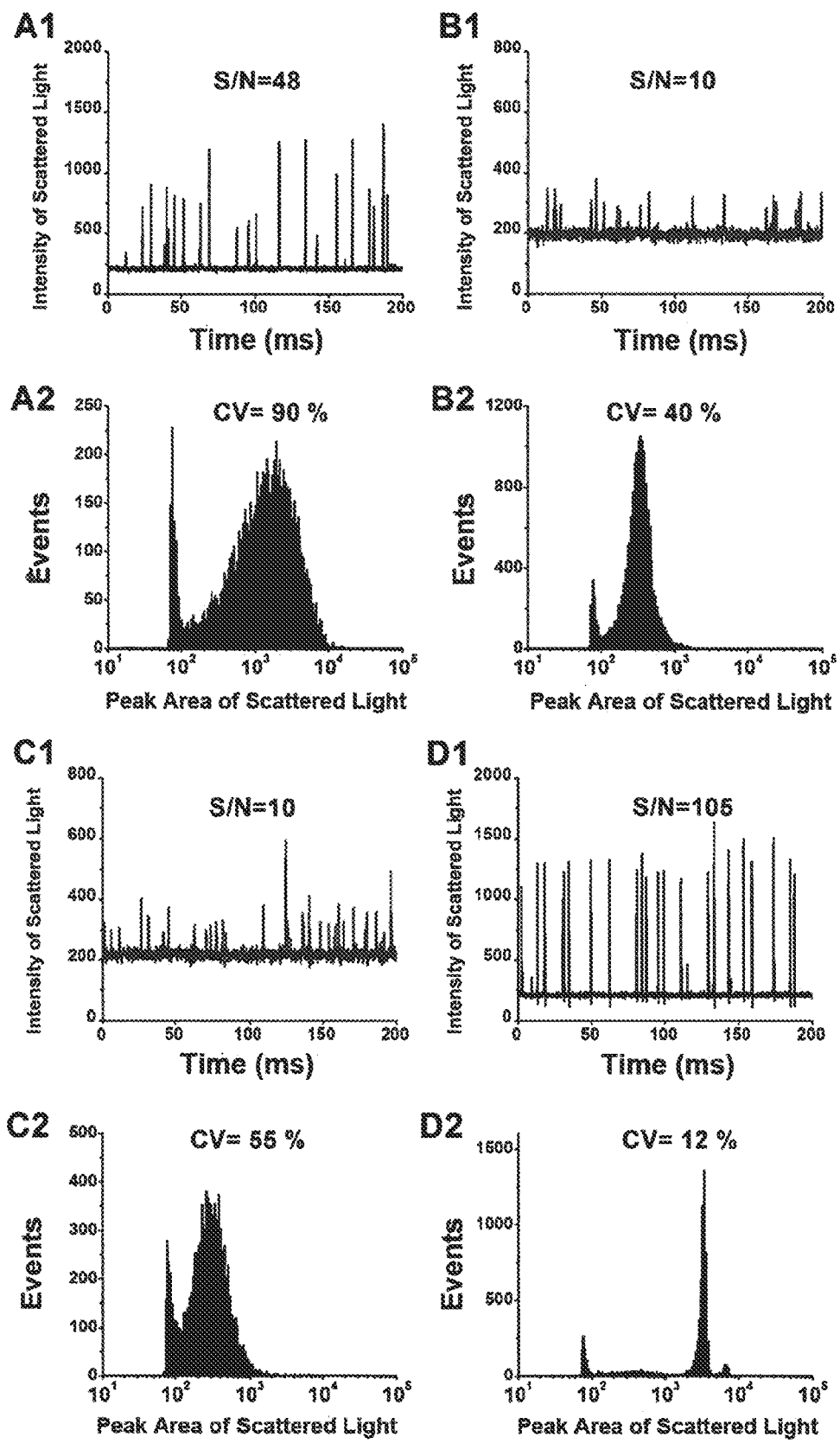

A relational diagram of the electrical signals obtained through conversion using an APD (serves as the photoelectric detector 7) vs. time is shown in FIG. 6A1. The S/N, which is a ratio of the peak height of scattered light after removing the background signals to the standard deviation of the background signals, is calculated as equal to 48. It can be seen from the result in FIG. 6A1: the scattered light of single polystyrene nano-particle with 44 nm particle size can be detected at a high S/N.

A frequency distribution histogram of the peak area of scattered light obtained through conversion using an APD (serves as the photoelectric detector 7) is shown in FIG. 6A2, wherein the peak of scattered light refers to the peak in the relational diagram of the electrical signals vs. time. A coefficient of variation (CV), which is a ratio of the standard deviation of peak area of scattered light to the average of peak area of scattered light, is calculated as equal to 90%. Based on the Mie scattering theory, in a case that the particle size is far smaller than the wavelength of the exciting light, the scattered light from the nano-particles is proportional to sixth-power of the particle size. Thus, a CV of particle size distribution can be obtained, i.e.

$$CV = \left(\sqrt[6]{(1+90\%)} - 1\right) \times 100\% = 11.3\%.$$

That value is essentially the same as the CV (9.1%) obtained with a TEM test method. Hence, it proves that the method provided in the present invention can be used to detect the particle size distribution of 44 nm polystyrene nano-spheres and can obtain an authentic detection result.

Comparative Example 1

The measurement is made with the method described in the example 1, but the difference is: the volumetric flow rate of the sample liquid in sample tube 2 is 20 nL/min, and the flow velocity of the sheath fluid 13 is 20 cm/sec, i.e. the sectional radius of the sample liquid flow 14 is approx. 0.73 µm, and suppose R is 0.73 µm, ω is 8 µm, the volume of the detecting region is 26.8 fL, the duration of irradiation of the measuring light on single nano-particle in the sample liquid flow is 0.08 ms.

In the relational diagram of the electrical signals obtained through conversion using an APD (serves as the photoelectric detector 7) vs. time, it is unable to distinguish the signals from the background noise.

Comparative Example 2

The measurement is made with the method described in the example 1, but the difference is: a PMT (R928 from Hamamatsu) with an 8×24 mm photosensitive region is selected as the photoelectric detector 7, and the photosensitive region of the PMT is arranged at the same position as the photosensitive region of the APD in example 1. The area of the photosensitive region of the PMT is $1.92 \times 10^8$ µm$^2$, and the stray light can't be removed, i.e. optical spatial filtering is not carried out.

In the relational diagram of the electrical signals obtained through conversion using a PMT (serves as the photoelectric detector 7) vs. time, it is unable to distinguish the signal from the background noise.

The results in example 1 and comparative examples 1-2 indicate that the method provided in the present invention can realize high-sensitivity detection of the scattered light from a single nano-particle by controlling the duration of irradiation of the measuring light on single nano-particle in the sample liquid flow to 0.1-10 ms and filtering out the light signals outside the detecting region.

Example 2

The measurement is made with the method described in the example 1, but the difference is: the sample liquid to be tested is a suspension liquid of silicon dioxide nano-spheres with 40 nm particle size at a concentration of $2 \times 10^9$ particles/mL.

The relational diagram of the electrical signals obtained through conversion using an APD (serves as the photoelectric detector 7) vs. time is shown in FIG. 6B1, and the calculated S/N is 10. It can be seen from the result in FIG. 6B1: the scattered light from a single silicon dioxide nano-sphere with 40 nm particle size can be clearly distinguished from the background.

The frequency distribution histogram of the peak area of scattered light obtained through conversion using an APD (serves as the photoelectric detector 7) is shown in FIG. 6B2, and the calculated CV is 40%. Based on the Mie scattering theory, a CV of particle size distribution can be obtained, i.e.

$$CV = \left(\sqrt[6]{(1+40\%)} - 1\right) \times 100\% = 5.8\%.$$

That value is essentially the same as the CV (4.8%) obtained with a TEM test method. Hence, it proves that the method provided in the present invention can be used to detect the particle size distribution of 40 nm silicon dioxide nano-spheres and can obtain an authentic detection result.

Example 3

The measurement is made with the method described in the example 1, but the difference is: the sample liquid to be tested is a suspension liquid of gold nano-particles with 10 nm particle size at a concentration of $2 \times 10^9$ particles/mL.

The relational diagram of the electrical signal obtained through conversion using an APD (serves as the photoelectric detector 7) vs. time is shown in FIG. 6C1, and the calculated S/N is 10. It can be seen from the result in FIG. 6C1: the scattered light from a single gold nano-particle with 10 nm particle size can be clearly distinguished from the background.

The frequency distribution histogram of the peak area of scattered light obtained through conversion using an APD (serves as the photoelectric detector 7) is shown in FIG. 6C2, and the calculated CV is 55%. Based on the Mie scattering theory, a CV of particle size distribution can be obtained, i.e.

$$CV = \left(\sqrt[6]{(1 + 55\%)} - 1\right) \times 100\% = 7.6\%.$$

That value is essentially the same as the CV (7.1%) obtained with a TEM test method specified by the manufacturer. Hence, it proves that the method provided in the present invention can be used to detect the particle size distribution of 10 nm gold nano-particles and can obtain an authentic detection result.

Example 4

The measurement is made with the method described in the example 1, but the difference is: the sample liquid to be tested is a suspension liquid of T7 bacteriophages at a concentration of $2 \times 10^9$ particles/mL.

The relational diagram of the electrical signal obtained through conversion using an APD (serves as the photoelectric detector 7) vs. time is shown in FIG. 6D1, and the calculated S/N is 105. It can be seen from the result in FIG. 6D1: the scattered light from a single T7 bacteriophage can be detected at a high S/N.

The frequency distribution histogram of the peak area of scattered light obtained through conversion using an APD (serves as the photoelectric detector 7) is shown in FIG. 6D2, and the calculated CV is 12%. Based on the Mie scattering theory, a CV of particle size distribution can be obtained, i.e.

$$CV = \left(\sqrt[6]{(1 + 12\%)} - 1\right) \times 100\% = 1.9\%.$$

On condition that there is no difference in particle size among natural T7 bacteriophages, the systematic error of the method provided in the present invention for particle size detection is 1.9%.

Example 5

Silicon dioxide nano-spheres with particle size of 40 nm, 50 nm, 60 nm, 78 nm and 90 nm at a concentration of $2 \times 10^9$ particles/mL with equal volume are mixed to obtain a mixed silicon dioxide nano-sphere sample. The measurement is made with the method described in the example 1, but the difference is: the sample liquid to be tested is the mixed silicon dioxide nano-sphere sample described above.

Figure 8:
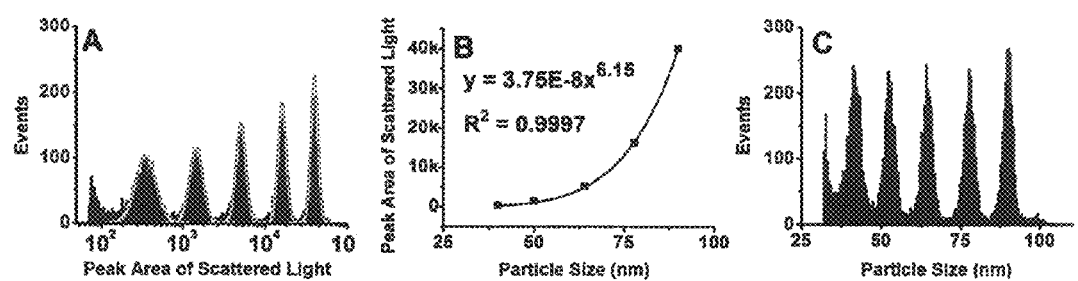
FIG. 8A shows the detection results in the form of a distribution histogram of peak area of scattered light of a mixed sample of 40 nm, 50 nm, 64 nm, 78 nm, and 90 nm silicon dioxide nano-spheres in example 5.
FIG. 8B is a diagram illustrating the relation between the median of Gaussian fitted peak area of scattered light and the average particle size measured by TEM of the mixed sample referenced in FIG. 8A.
FIG. 8C is a particle size distribution histogram of the mixed sample after scattered light peak area—particle size conversion.

The frequency distribution histogram of the photon burst peak areas of scattered light obtained through conversion using an APD (serves as the photoelectric detector 7) is shown in FIG. 8A. It can be seen that the photon burst peak areas of the scattered light clearly exhibit 5 peaks, which correspond to five types of silicon dioxide nano-spheres with different particle size.

Relational curves of the median of peak area of scattered light from silicon dioxide nano-spheres vs. the particle size of each silicon dioxide nano-spheres are fitted for the five types of silicon dioxide nano-spheres with different particle size, as shown in FIG. 8B, with a curve equation $y=3.75e-8x^{6.15}$, wherein y represents the peak area of scattered light, x represents the particle size. The $R^2$ is as high as 0.9997, indicating the peak area of scattered light is proportional to the 6.15' power of the particle size of silicon dioxide nano-spheres, which matches well the sixth-power declared in the Mie scattering theory.

With the equation $y=3.75e-8x^{6.15}$, the photon burst peak areas of scattered light from the silicon dioxide nano-spheres are converted into particle size, and the frequency distribution histograms of particle size are shown in FIG. 8C. It can be seen that the results are quite similar to the results of particle size distribution (FIG. 7F) of the five types of nano-particles obtained with a TEM test method respectively, which indicates that the method provided in the present invention accurately characterizes the particle size distributions of the five types of silicon dioxide nano-spheres with different particle size in the mixed silicon dioxide nano-spheres sample.

Example 6

The measurement is made with the method described in the example 1, but the difference is: laser with 532 nm wavelength is focused through a lens 1 (C330TM-A from Thorlabs) into a laser beam 12 with 6.4 μm beam waist diameter, the irradiation intensity is 498 kW/cm² at the position of beam waist. Please see FIG. 2, suppose R is 0.73 μm, ω is 3.2 μm, then the calculated volume of the detecting region is 10.7 fL, and the duration of irradiation of the measuring light on single nano-particle in the sample liquid flow is 0.3 ms. The sample liquid to be tested is a suspension liquid of gold nano-particles with 6.7 nm particle size at a concentration of $2 \times 10^9$ particles/mL.

Figure 10:
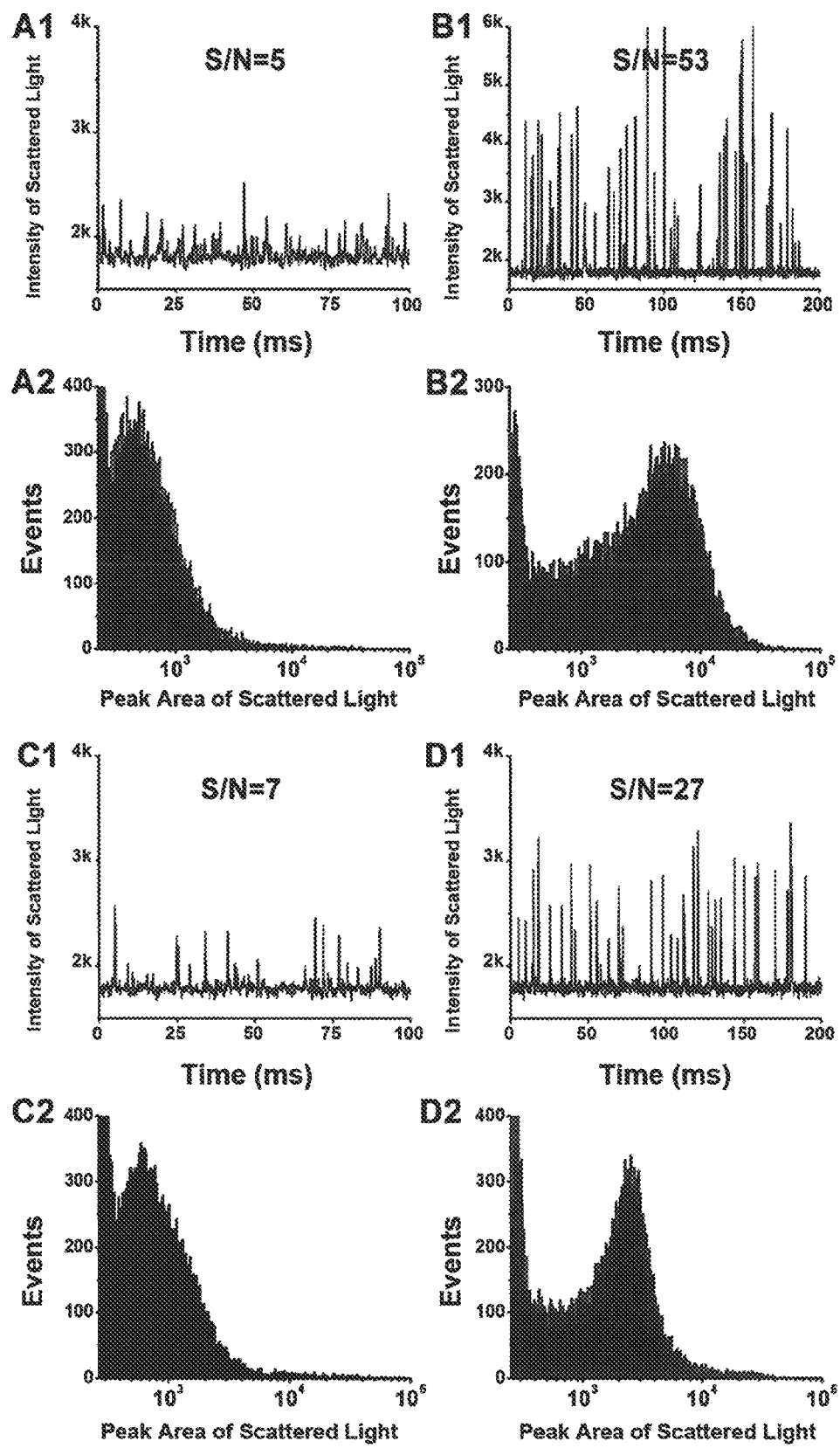

The relational diagram of the electrical signals obtained through conversion using an APD (serves as the photoelectric detector 7) vs. time is shown in FIG. 10A1, and the calculated S/N is 5. It can be seen from the result in FIG. 10A: the scattered light from a single gold nano-particle with 6.7 nm particle size can be opportunely distinguished from the background.

Example 7

The measurement is made with the method described in the example 6, but the difference is: the sample liquid to be tested is a suspension liquid of gold nano-particles with 10 nm particle size at a concentration of $2 \times 10^9$ particles/mL.

The relational diagram of the electrical signals obtained through conversion using an APD (serves as the photoelectric detector 7) vs. time is shown in FIG. 10B1, and the calculated S/N is 53. It can be seen from the result in FIG. 10B: the scattered light from a single gold nano-particle with 10 nm particle size can be clearly distinguished from the background.

The results in examples 3, 6, and 7 indicate that the method provided in the present invention can effectively improve the sensitivity of detection of the scattered light from a single nano-particle and thereby attain a lower detection limit by enhancing the irradiation intensity at the position of beam waist.

Example 8

The measurement is made with the method described in the example 6, but the difference is: the sample liquid to be tested is a suspension liquid of silicon dioxide nano-spheres with 24 nm particle size at a concentration of $2 \times 10^9$ particles/mL.

The relational diagram of the electrical signals obtained through conversion using an APD (serves as the photoelectric detector 7) vs. time is shown in FIG. 10C1, and the calculated S/N is 7. It can be seen from the result in FIG. 10C: the scattered light from a single silicon dioxide nano-sphere with 24 nm particle size can be opportunely distinguished from the background.

Example 9

The measurement is made with the method described in the example 6, but the difference is: the sample liquid to be tested is a suspension liquid of silicon dioxide nano-spheres with 29 nm particle size at a concentration of $2 \times 10^9$ particles/mL.

The relational diagram of the electrical signals obtained through conversion using an APD (serves as the photoelectric detector 7) vs. time is shown in FIG. 10D1, and the calculated S/N is 27. It can be seen from the result in FIG. 10D: the scattered light from a single silicon dioxide nano-sphere with 29 nm particle size can be clearly distinguished from the background.

In connection with the above description, it will be appreciated that FIG. 7A shows a TEM image of 40 nm silicon dioxide nano-spheres in examples 2 and 5; FIG. 7B shows a TEM image of 50 nm silicon dioxide nano-spheres in example 5; FIG. 7C shows a TEM image of 64 nm silicon dioxide nano-spheres in example 5; FIG. 7D shows a TEM image of 78 nm silicon dioxide nano-spheres in example 5; FIG. 7E shows a TEM image of 90 nm silicon dioxide nano-spheres in example 5; and FIG. 7F shows particle average size and particle size distribution diagrams of each type of nano-particles obtained by performing statistics on the particle size of 150 nano-particles respectively;

In addition, FIG. 9A shows a TEM image of 24 nm silicon dioxide nano-spheres in example 8; FIG. 9B shows a TEM image of 29 nm silicon dioxide nano-spheres in example 9;

Also, FIG. 10A1, FIG. 10B1, FIG. 10C1 and FIG. 10D1 show the detection results in the form of signal waveform diagrams of scattered light channels for the samples in examples 6-9 of 6.7 nm gold nano-particles, 10 nm gold nano-particles, 24 nm silicon dioxide nano-spheres, and 29 nm silicon dioxide nano-spheres respectively; and FIG. 10A2, FIG. 10B2, FIG. 10C2 and FIG. 10D2 are frequency distribution histograms of peak area of scattered light for the samples in examples 6-9.

While some preferred embodiments of the present invention are described above with reference to the accompanying drawings, the present invention is not limited to the details in those embodiments. Those skilled in the art can make modifications and variations to the technical solution of the present invention, without departing from the spirit of the present invention. However, all these modifications and variations shall be deemed as falling into the protected range of the present invention. For example, the objective can be substituted with a simple lens.

In addition, it should be noted that the specific technical features described in above mentioned embodiments can be combined in any appropriate form, provided that there is no conflict. To avoid unnecessary repetition, the possible combinations are not described specifically in the present invention.

The invention claimed is:

1. A method for detecting nano-particles, comprising the following steps:
   (1) compressing a sample liquid to be detected into a sample liquid flow by hydrodynamic focusing using a sheath fluid, wherein the sample liquid flow contains nano-particles to be detected, and the nano-particles are essentially separated from each other and essentially flow in the same line in the sample liquid flow;
   (2) irradiating a measuring light to the sample liquid flow, wherein a single nano-particle in the sample liquid flow is irradiated by the measuring light for 0.1-10 ms, preferably 0.2-2 ms;
   (3) defining the region of the sample liquid flow subjected to irradiation of the measuring light as a detecting region, and collecting light signals emitted from the region irradiated by the measuring light via a lens imaging system, and allowing the light signals collected by the lens imaging system to pass through a field stop, so as to filter out the light signals outside the detecting region and enrich the light signals from the detecting region, the volume of the detecting region is 1-100 fL, preferably 10-100 fL, more preferably 10-30 fL;
   (4) subjecting the light signals enriched by the field stop to optoelectronic signal conversion, and acquiring the electrical signals of scattered light emitted from each nano-particle in the sample liquid flow, or the electrical signals of scattered light and fluorescent light emitted from each nano-particle in the sample liquid flow, the field stop is a photosensitive region of a photoelectric detector or an aperture diaphragm added in front of the photoelectric detector, the area of the photosensitive region or the aperture area of the aperture diaphragm is 50 to $5 \times 10^6$ μm$^2$, preferably $2 \times 10^3$ to $2 \times 10^5$ μm$^2$, more preferably $8 \times 10^3$ to $8 \times 10^4$ μm$^2$;
   (5) carrying out qualitative and/or quantitative analysis for the nano-particles according to the electrical signals.

2. The method according to claim 1, wherein the diameter of the sample liquid flow is 0.1-20 μm, preferably 0.5-5 μm, more preferably 1-3 μm.

3. The method according to claim 1, wherein the volumetric flow rate of the sample liquid flow is 0.1-100 nL/min, preferably 0.5-30 nL/min, more preferably 1-5 nL/min.

4. The method according to claim 1, wherein the flow velocity of the sheath fluid is 0.5-10 cm/sec, preferably 1-3 cm/sec, more preferably 1.2-2.5 cm/sec.

5. The method according to claim 1, wherein the beam diameter of the measuring light is 1-150 times of the diameter of the sample liquid flow, preferably 2-50 times, more preferably 5-20 times.

6. The method according to claim 1, wherein the intensity of the measuring light is 0.05-8,000 kW/cm$^2$, preferably 0.5-5,000 kW/cm$^2$, more preferably 10-1,000 kW/cm$^2$.

7. The method according to claim 1, wherein the lens imaging system is an infinity-corrected optical system or finity-corrected optical system.

8. The method according to claim 7, wherein the infinity-corrected optical system comprises infinite objective and imaging lens, while the finity-corrected optical system comprises a finite objective.

9. The method according to claim 1, wherein the photoelectric signal conversion is implemented with a photoelectric detector, which, for example, includes but is not limited to avalanche photodiode, photomultiplier tube, silicon photodiode, charge coupling element or complementary metal oxide semiconductor device, and preferably, the photoelectric detector is an avalanche photodiode.

10. The method according to claim 1, wherein the particle size of the nano-particles is 1-1,000 nm, preferably 5-200 nm, more preferably 6.7-100 nm.

11. The method according to claim 1, wherein the nano-particles are artificially synthesized or natural nano-particles, and the natural nano-particles preferably are at least one type of biological nano-particles among prokaryotic cells, organelles and viruses, etc.

12. The method according to claim 2, wherein the volumetric flow rate of the sample liquid flow is 0.1-100 nL/min, preferably 0.5-30 nL/min, more preferably 1-5 nL/min.

13. The method according to claim 5, wherein the intensity of the measuring light is 0.05-8,000 kW/cm$^2$, preferably 0.5-5,000 kW/cm$^2$, more preferably 10-1,000 kW/cm$^2$.

14. The method according to claim 12, wherein the flow velocity of the sheath fluid is 0.5-10 cm/sec, preferably 1-3 cm/sec, more preferably 1.2-2.5 cm/sec; the beam diameter of the measuring light is 1-150 times of the diameter of the sample liquid flow, preferably 2-50 times, more preferably 5-20 times; the intensity of the measuring light is 0.05-8,000 kW/cm2, preferably 0.5-5,000 kW/cm2, more preferably 10-1,000 kW/cm2.

\* \* \* \* \*